United States Patent [19]

Cousins et al.

[11] Patent Number: 4,484,778

[45] Date of Patent: Nov. 27, 1984

[54] SHAPEABLE MATRIX, AND A CHAIR USING A MATRIX

[75] Inventors: Steven J. Cousins, Ashtead; Keith N. Jones, Carshalton Beeches; Kenneth E. Ackerley, East Croydon, all of England

[73] Assignee: University College London, London, England

[21] Appl. No.: 362,272

[22] Filed: Mar. 26, 1982

[30] Foreign Application Priority Data

Mar. 31, 1981 [GB] United Kingdom ............... 8109998

[51] Int. Cl.³ .............................................. A47C 3/00
[52] U.S. Cl. .................................. 297/284; 403/143; 297/458; 297/459; 297/460; 446/124
[58] Field of Search ............... 403/57, 58, 64, 76, 403/77, 217, 218, 171, 172, 125, 90, 126, 132, 133, 135, 141, 143; 46/15, 16, 23; 297/284, 458, 459, 460

[56] References Cited

U.S. PATENT DOCUMENTS

| | | | |
|---|---|---|---|
| 2,373,802 | 4/1945 | Anderson | 128/90 |
| 3,299,721 | 1/1967 | Ziegler | 403/143 |
| 3,310,906 | 3/1967 | Glukes | 46/23 X |
| 3,379,472 | 4/1968 | Hilfiker | 297/284 X |
| 3,565,482 | 2/1971 | Blodee | 297/284 |
| 3,583,091 | 6/1971 | Brockway | 46/16 |
| 3,822,499 | 7/1974 | Devos | 5/465 |
| 4,142,816 | 3/1979 | Kramer | 403/143 |
| 4,145,083 | 3/1979 | Urban | 297/284 |
| 4,295,683 | 10/1981 | Dubbink et al. | 297/458 |
| 4,347,840 | 9/1982 | Adams | 297/284 |
| 4,367,897 | 1/1983 | Cousins | 297/284 X |

FOREIGN PATENT DOCUMENTS

| | | |
|---|---|---|
| 664804 | 2/1965 | Belgium ............................ 403/143 |
| 2146809 | 3/1973 | Fed. Rep. of Germany .......... 46/23 |
| 1532378 | 6/1968 | France . |
| 2123609 | 9/1972 | France . |
| 2196134 | 3/1974 | France . |
| WO80/00541 | 3/1980 | PCT Int'l Appl. . |
| 354015 | 6/1961 | Switzerland ........................... 46/23 |
| 1421502 | 1/1976 | United Kingdom . |

Primary Examiner—James T. McCall
Attorney, Agent, or Firm—McAulay, Fields, Fisher, Goldstein & Nissen

[57] ABSTRACT

A shapeable matrix comprises a plurality of first members each of which has a plurality of projections located on the periphery thereof, and a plurality of second members each of which has a plurality of recesses located on the periphery thereof, each recess being adapted to receive a respective one of the projections of an adjacent first member. Means are provided on each of the second members for releasably clamping the projections of the first members in recesses of the second members, the clamping being operative in a released condition to permit alteration in the relative orientation of adjacent members and being operative in a clamped condition to prevent such alteration. A chair is disclosed which comprises a support frame and a shapeable matrix as set forth above mounted on the support frame.

7 Claims, 7 Drawing Figures

SHAPEABLE MATRIX, AND A CHAIR USING A MATRIX

FIELD OF THE INVENTION

This invention relates to a shapeable matrix and to an adjustable seat formed from such a matrix, more particularly for a handicapped person, and especially for a handicapped child. It should be added, however, that the shapeable matrix of this invention has applications other than in the making of an adjustable seat, as will become apparent from the following description.

BACKGROUND OF THE INVENTION

Many disabled children, such as those suffering from cerebral palsy and muscular dystrophy for example, need additional support when occupying a wheelchair, as otherwise they cannot remain erect or properly seated and may even go into spasm with the result thay they fall or at least collapse into an uncomfortable and sometimes dangerous position if not securely strapped into the chair. Improperly seated children tend to develop pressure sores and there is a risk of increased spinal deformaties and respiration difficulties which make it risky to leave a disabled child unattended in a conventional wheelchair or the like.

There are a number of chairs presently available which are designed so that the shape of the seat and back portions of the chair can be altered to make an able bodied person, and particularly an adult, more comfortable and less subjected to fatigue, but these are of little help when it comes to providing the type of seating which is required by disabled adults and children. When attempts are made to incorporate some of the structural features of known chairs into a specialized seat for a disabled person, it is generally found that such a seat is expensive and requires a considerable amount of the time of a skilled technician attempting to fabricate and adjust the seat to meet the needs of particular individuals. The result has been that some treatment and rehabilitation centres have restored to making seat inserts for conventional chairs. Such inserts are often cast of plaster or are otherwise formed to fit a particular child and are discarded and replaced periodically as the intended user grows or his condition changes.

BRIEF SUMMARY OF THE INVENTION

According to the present invention there is provided a shapeable matrix comprising a plurality of first members each of which has a plurality of projections located on the periphery thereof, and a plurality of second members each of which has a plurality of recesses located on the periphery thereof, each recess being adapted to receive a respective one of the projections of an adjacent first member, and means provided on each of the second members for releasably clamping the projections of the first members in recesses of the second members, the clamping being operative in a released condition to permit alteration in the relative orientation of adjacent members and being operative in a clamped condition to prevent such alteration.

The invention further provides a chair which comprises a support frame and a shapeable matrix as set forth above mounted on the support frame.

DETAILED DESCRIPTION OF ILLUSTRATED EMBODIMENTS

Figure 1:
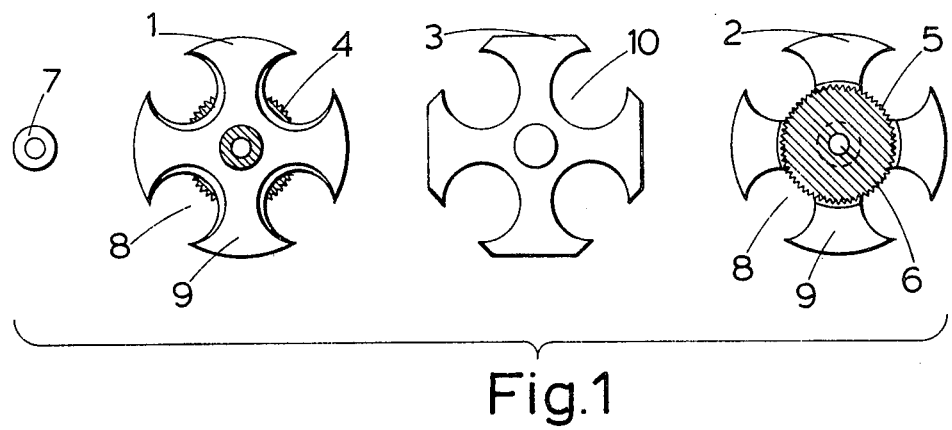
FIG. 1 shows a second member in disassembled form.

The form of second member shown in FIG. 1 comprises a plastic disc 1, a plastic disc 2, and a metal plate 3 sandwiched between them. On the outside of the assembly of discs 1 and 2 and plate 3 are metal discs 4 and 5 which have serrated edges. The disc 5 is formed with a downwardly extending rivet 6 which is threaded on the inside, and second member is held together by a screw, preferably a Philips headed screw 7, which threadedly engages the thread in the rivet 6. Each plastic disc has four recesses 8 formed in the periphery thereof, and spaced by 90° from one another, the recesses defining arms 9 therebetween. The thickness of each arm decreases outwardly. Although four recesses are shown the number could be more or less if desired. The metal plate 3 has four corresponding recesses 10. When the second member is assembled the recesses of the plastics disc and metal plate together define part-spherical recesses.

Figure 2:
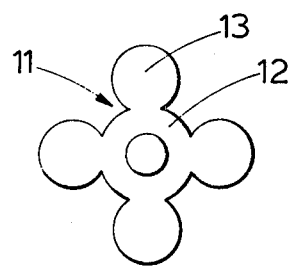
FIG. 2 shows a plan view of a first member.

The first member 11 shown in FIG. 2 comprises a cylindrical portion 12 with four substantially spherical projections 13 on the periphery thereof at 90° to one another. The member 11 is of a plastic material.

Figure 3:
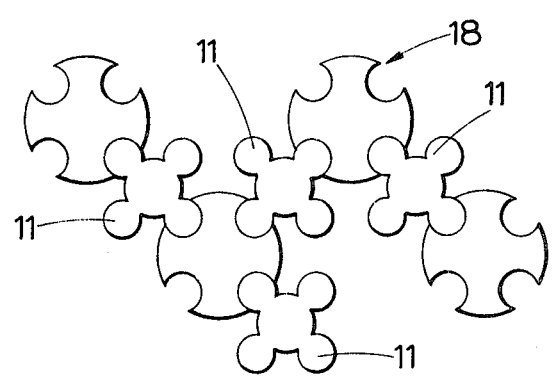
FIG. 3 is a sketch view of part of a matrix formed from the members shown in FIGS. 1 and 2.

A shapeable matrix is formed by assembling a plurality of first and second members together. A small portion of a matrix is shown in FIG. 3 and denoted as 18. The matrix is formed by clamping projections of the first members in respective ones of the part-spherical recesses of the second members. This is done by engaging the disassembled parts of a second member with a first member so that a projection of the first member is located in a part-spherical recess of the second member, and then inserting and tightening the screw 7 of the second member with the first and second members in the desired orientation. It will be understood that the matrix of first and second members is connected together by what is effectively a plurality of universal joints which permit adjacent first and second members to be orientated within a wide range of angles with respect to one another. The clamping of adjacent first and second members is ensured by the metal discs 4 and 5 the serrations of which bite into the projections 13. The metal plate 3 serves to provide the second member with the necessary rigidity.

Not only can the matrix be of any desired planar form, it can also extend in more than one plane. For example, if it is desired to provide additional rigidity a row of first members can be orientated so that the major plane thereof is perpendicular to the major plane of the adjacent second members and a subsidiary matrix of first and second members can be attached to projections of the row of first members to form a rib extending in a plane at right angles to the adjacent part of the main matrix.

Figure 4:
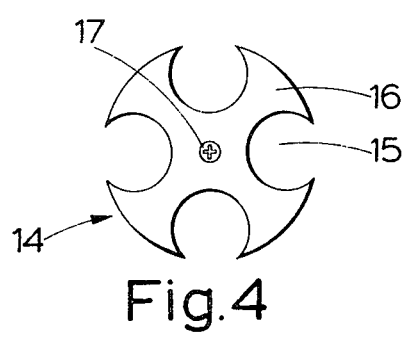
FIG. 4 shows a modified form of second member.

An alternative, simpler, form of second member is shown in FIG. 4. This comprises a pair of metal discs 14 having recesses 15 and arms 16. The arms of the discs are curved towards one another so that the discs define between them four part-spherical recesses. The metal discs are held together by a screw 17 which engages in a threaded rivet in the opposite disc (not shown).

The plastic material used in the first and second members can conveniently be acetal, and the metal can conveniently be aluminium alloy.

Figure 5:
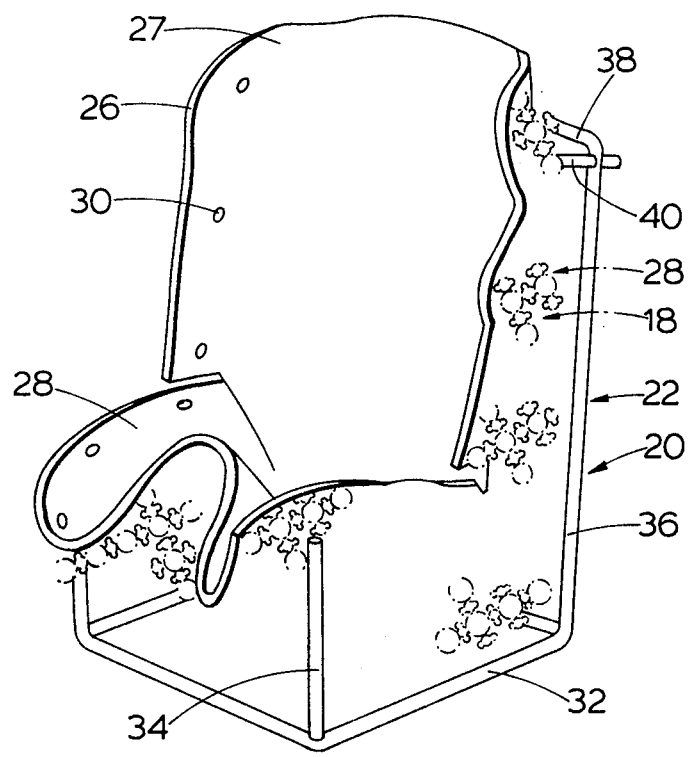
FIG. 5 shows a chair constructed using the matrix of FIG. 3.

An adjustable seat can readily be formed using the shapeable matrix described above by mounting the matrix in a support frame and, preferably, putting a cover, for example a padded cover, over the matrix. An example of such a seat is shown in FIG. 5. This shows an adjustable seat 20 provided with a suitable support frame 22 which carries a shapeable matrix 18. A flexible padded cover 26 is provided on one side of the matrix and this cover is shaped along with the matrix to provide the seat with a back portion 27 and a seat portion 28. The pad 26 is secured to the matrix at widely-spaced intervals. For example, it may be releasably attached along side edges of the two layers by means of ties 30.

In order to carry the padded matrix, the support frame generally indicated at 22 is constructed of lengths of aluminium tubing which are connected together to provide a horizontal base 32. The front and rear corner posts 34 and 36 are mounted on this base. A cross bar 38 extends between the tops of the rear corner posts of the frame. The upper ends of the short front corner posts 34 as well as those on the relatively long rear corner posts 36 each carry a horizontally disposed hanger 40 which extends inwardly of the base frame. The matrix is suspended from these hangers out of contact with the remainder of the frame. The chair can readily be adjusted by loosening the screws 7 or 17, forming the matrix into the desired shape and then retightening the screws. Furthermore, the chair can readily be enlarged by adding further first and second members to the matrix, or of course it can be reduced in size by taking members away.

Figure 6:
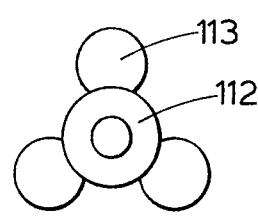
FIG. 6 shows another modified form of first member.
Figure 7:
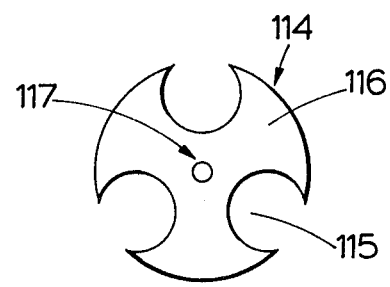
FIG. 7 shows a second member for use with the member of FIG. 6.

An alternative geometric configuration of the members shown in FIGS. 2 and 4 is shown in FIGS. 6 and 7. The member shown in FIG. 6 comprises a central cylindrical portion 112 with three substantially spherical projections 113 on the periphery thereof at 120° to one another. The second member shown in FIG. 7 comprises a pair of metal discs 114 having recesses 115 and arms 116. The recesses are 120° apart. The arms of the discs are curved towards one another so that the discs define between them three part-spherical recesses. The metal discs are held together by a screw 117 which engages in a threaded rivet in the opposite disc (not shown).

The three ball member and clamp is particularly applicable for adjustable sockets for children and geriatric age group amputees, and also for fracture bracing as a replacement for plaster of Paris.

We claim:

1. A shapeable matrix comprising a plurality of first members each of which has a plurality of projections located on the periphery thereof, and a plurality of second members each of which has a plurality of recesses located on the periphery thereof, each recess being adapted to receive a respective one of the projections of an adjacent first member, and means provided on each of the second members for releasably clamping the projections of the first members in recesses of the second members, the clamping being operative in a released condition to permit each projection and is associated recess to act as a univeral joint and thereby to permit alteration in the relative orientation of adjacent members and being operative in a clamped condition to prevent such alteration.

2. A matrix according to claim 1, wherein each said first member comprises a central portion and a plurality of substantially spherical projections extending from the periphery of the central portion.

3. A matrix according to claim 1, wherein each said second member comprises a pair of plastic discs with a metal plate sandwiched between them, the discs and plate each having a plurality of openings in the periphery thereof which together define the said plurality of recesses.

4. A matrix according to claim 3, further comprising a pair of metal discs each sandwiched between the said metal plate and a respective one of the plastic discs, the said metal discs having serrated edges and being of such a size that the serrated edges engage in the said projections of the first member.

5. A matrix according to claim 1, wherein each first member has four projections arranged at 90° to one another, and each second member has four recesses arranged at 90° to one another.

6. A matrix according to claim 1, wherein each first member has three projections arranged at 120° to one another, and each second projection has three recesses arranged at 120° to one another.

7. A chair which comprises a support frame; and a shapeable matrix mounted on the frame, the shapeable matrix comprising a plurality of first members each of which has a plurality of projections located on the periphery thereof, and a plurality of second members each of which has a plurality of recesses located on the periphery thereof, each recess being adapted to receive a respective one of the projections of an adjacent first member, and means provided on each of the second members for releasably clamping the projections of the first members in recesses of the second members, the clamping being operative in a released condition to permit each projection and its associated recess to act as a universal joint and thereby to permit alteration in the relative orientation of adjacent members and being operative in a clamped condition to prevent such alteration.

* * * * *